United States Patent [19]
> Gallagher, Jr.
>
> [11] Patent Number: 4,588,740
> [45] Date of Patent: May 13, 1986

[54] PHARMACEUTICAL METHODS USING 4-AMINOALKYL-2(3H)-INDOLONES

[75] Inventor: Gregory Gallagher, Jr., Jeffersonville, Pa.

[73] Assignee: SmithKline Beckman Corporation, Philadelphia, Pa.

[21] Appl. No.: 597,006

[22] Filed: Apr. 5, 1984

Related U.S. Application Data

[63] Continuation-in-part of Ser. No. 447,564, Dec. 7, 1982, Pat. No. 4,452,808.

[30] Foreign Application Priority Data

Nov. 17, 1983 [CA] Canada ............................... 441416

[51] Int. Cl.⁴ .................... A61K 31/40; C07D 209/32
[52] U.S. Cl. .................................... 514/418; 548/486
[58] Field of Search ................. 548/486; 424/272; 514/418

[56] References Cited

U.S. PATENT DOCUMENTS

| | | | |
|---|---|---|---|
| 3,573,310 | 3/1971 | Van Dyke | 548/486 |
| 4,148,895 | 4/1979 | Lattrell | 548/483 |
| 4,314,944 | 2/1982 | Huffman | 548/486 |
| 4,452,808 | 6/1984 | Gallager | 548/486 |

FOREIGN PATENT DOCUMENTS

| | | | |
|---|---|---|---|
| 895875 | 3/1972 | Canada | 548/486 |
| 7223538 | 6/1972 | Japan | 548/486 |

Primary Examiner—Donald G. Daus
Assistant Examiner—G. Hendricks
Attorney, Agent, or Firm—William H. Edgerton; Richard D. Foggio; Alan D. Lourie

[57] ABSTRACT

A series of pharmaceutical compositions which contain 4-aminoalkyl-2(3H)-indolones has been demonstrated to have $D_2$-agonist activity useful for treating congestive heart failure and hypertension. A representative ingredient of the compositions is 4-di-n-propylaminoethyl-2(3H)-indolone or a salt thereof.

13 Claims, No Drawings

PHARMACEUTICAL METHODS USING 4-AMINOALKYL-2(3H)-INDOLONES

This is a continuation-in-part application of Ser. No. 447,564 filed Dec. 7, 1982, now U.S. Pat. No. 4,452,808 issued June 5, 1984.

This invention relates to novel 4-aminoalkyl-4(3H)-indolones having anti-hypertensive or anti-anginal activity.

4-Aminoalkyl-7-hydroxy-2(3H)-indolones were described in U.S. Pat. No. 4,314,944 to have a beneficial effect on certain abnormal conditions of the cardiovascular system. More specifically, such compounds were said to have a vasodilatation effect on the kidney which is similar to that of dopamine, thereby inducing anti-hypertensive activity due to the renal dopaminergic activity.

The basic structure of the prior art compounds is similar to that of the well known cardiovascular agent they mimic, dopamine:

U.S. Pat. No. 4,314,944

Dopamine

One skilled in the structure-function art will appreciate that the 7-hydroxy group of the compounds of the cited reference is necessary for their structures to resemble that of dopamine. Without this key substituent, the resulting compounds would not be expected to have cardiovascular activity.

Unexpectedly, the indolone compounds of this invention have beneficial cardiovascular activity despite the lack of the supposedly essential 7-hydroxy group. In addition to not having a catechol or catechol-mimicking structure, these indolones may not be subject to tachyphylaxis and are better absorbed orally when compared with the 7-hydroxy compounds.

The compounds of this invention are illustrated by the following structural formula:

I in which:

R is, each, hydrogen, lower alkyl, benzyl, allyl, phenethyl or 4-hydroxyphenethyl;

$R^1$, $R^2$ or $R^3$ are, each, hydrogen or lower alkyl; and n is 1–3.

A subgeneric group of this invention comprises the compounds of formula I in which:

$N(R)_2$ is amino, di-n-propylamino, n-propyl-n-butylamino or n-propyl-4-hydroxyphenethylamino;

$R^1$, $R^2$ or $R^3$ are hydrogen; and $(CH_2)_n$ is ethylene ($-CH_2-CH_2-$).

Preferred species of this invention are 4-(2-di-n-propylaminoethyl)-2(3H)-indolone and 4-(n-propyl-4-hydroxyphenethylaminoethyl)-2(3H)-indolone or one of their pharmaceutically acceptable, acid addition salts.

The term "lower alkyl" used herein and in the claims is meant, for convenience, to include branched and straight chain groups of from 1–6 carbons, preferably n-propyl, for the alkyl in each R and from 1–4 carbons, preferably methyl, for each of $R^1$, $R^2$ and $R^3$. $R^1$, $R^2$ and $R^3$ are preferably, for ease of preparation, all the same.

The pharmaceutically acceptable acid addition salts having the utility of the free bases of formula I are part of this invention. These are prepared by methods well known to the art and are formed with both inorganic or organic acids, for example: maleic, fumaric, benzoic, ascorbic, pamoic, succinic, bismethylenesalicylic, methane sulfonic, ethane disulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic and, especially, methane sulfonic acid salts are conveniently used.

The compounds of this invention are prepared by the following reaction sequences:

Scheme A (1)     (2)

Scheme B (3)     (4)

(5)     (6)

-continued
Scheme B

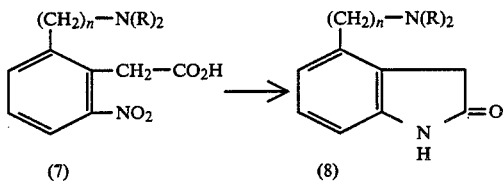

In the reaction sequences of Schemes A and B above, n, R, $R^1$, $R^2$ and $R^3$ are each as described for formula I; m is n−1. In some cases, such as where $N(R)_2$ is a primary or secondary amino, a protective group may be present, as described in more detail below.

In addition to the reaction sequences noted above, the compounds of this invention are prepared by the reactions which are described in U.S. Pat. No. 4,314,944 using, of course, known deshydroxy or desmethoxy starting materials. In preparing the present 7-unsubstituted indolones by this route, the ring closure to form the isatin ring at column 2 of that patent can proceed to give two isomeric products which must then be separated to yield the indolones of this invention.

In Scheme A, the corresponding 7-hydroxy indolone starting material (1) is de-hydroxylated by reacting it with at least a stoichiometric quantity of a reactive 5-halo-1-phenyl-1H-tetrazole, i.e. the 5-bromo, chloro or iodo-1-phenyl-1H-tetrazole, in the presence of an acid binding agent, such as an alkali metal carbonate, in a suitable inert solvent, such as aqueous acetone, dimethylformamide or dimethylacetamide. The reaction is carried out at room temperature until substantially complete. From one to two days may be used. If desired, the reaction may be carried out more quickly by operating at a higher temperature, for example, up to 75°.

The resulting new intermediate, a 4-(aminoalkyl)-7-(1-phenyl-1H-tetrazazol-5-yloxy)-2(3H)-indolone, is subjected to hydrogenation to split the tetrazole-oxyindolone link. Conveniently, catalytic hydrogenation using a noble metal catalyst at moderate pressures of hydrogen and some heat, such as palladium-on-charcoal at 50° for 20 hours under a low pressure of hydrogen, is used.

When $N(R)_2$ is a reactive amino, the starting material (1) is used in the form of an acid addition salt or an otherwise amino protected derivative. If a hydrogenation labile protective group is present on compound 1, it is also split during the reduction.

The reactions of Sequence B involve the insertion of the aminoalkyl side chain into the phenyl ring (1→7) followed by the critical ring closure of the o-carboxymethyl-m-nitro intermediate (7). The ring closure is carried out by reduction of the intermediate, for example, using catalytic hydrogenation over a noble metal, preferably palladium, catalyst in a suitable solvent, for example, a lower alcohol, dilute hydrochloric acid or glacial acetic acid, at low to moderate pressures of hydrogen and at a temperature chosen from the range of room temperature to 60°. The reaction proceeds quickly to completion. The nitro group of compound 7 is reduced first, followed by ring closure.

As noted above, this reaction sequence is adaptable to prepare the compounds having a reactive aminoalkyl side chain by protecting an amino or another reactive group with a standard protecting means such as forming a maleimide, tert.-boc or phthalimide derivative, which is removed, by standard reactions, after ring closure. The phthalimido protective group, for example, is split using reaction with hydrazine hydrate. A benzyloxy is split by using catalytic hydrogenation; a tert.-boc, using mild acid.

When a protected hydroxy group is present such as a methoxy or benzyloxy, it is removed by a demethylating agent such as boron tribromide or 48% hydrobromic acid. O-Benzyl groups are also split off using catalytic hydrogenation over a palladium catalyst.

The alkylated products of this invention are, alternatively, or, in certain instances, preferentially prepared by alkylation of the parent amino compounds of formula I in which $N(R)_2$ is amino or a secondary amino. For example, the N-alkylated products, formula I when $N(R)_2$ is a secondary or tertiary amino, are conveniently prepared by reductive alkylation using, for example, the aldehyde in one or two molar equivalent quantities under reduction conditions, such as under catalytic hydrogenation conditions over a palladium or platinum catalyst or such as using formaldehyde-formic acid when R is dimethylamino.

N-Alkylation, such as using an allyl or benzyl halide in the presence of an acid binding agent, can be used under standard mild conditions. Protecting the amido hydrogen in the ring is also used during alkylation if necessary as known to the art. Alkyl substituents at the 1 or 3-positions of the indolone ring are introduced by forming the lithio derivatives at the ring position, such as using butyl lithium, followed by reaction of the lithio compound with a lower alkyl halide, especially an alkyl iodide.

The compounds of this invention have utility, as specific dopamine agonists, in the treatment of disorders of the cardiovascular system, especially to treat hypertension, to treat angina pectoris, to treat the symptoms of congestive heart failure or to improve kidney function.

More specifically, the compounds of this invention, especially 4-(2-di-n-propylaminoethyl)-2(3H)-indolone hydrochloride, have proved to be selective peripheral $D_2$-agonists. Otherwise speaking, the main focus of action is at the presynaptic α-dopaminergic receptors which may also be called "$D_2$-receptors." Activation of the $D_2$-receptors on the sympathetic nerve terminals inhibits the release of norepinephrine, thereby, promoting vasodilation, among other beneficial cardiovascular actions and decreasing sympathetic side-effects caused by norepinephrine release in certain abnormal cardiovascular conditions.

In the perfused rabbit ear artery test, 4-(2-di-n-propylaminoethyl)-2(3H)-indolone hydrochloride had an $EC_{50}$ of 72 nM. It was active in vivo in the dog in both the cardio-accelerator nerve and perfused hind limb preparations and did not cause tachyphylaxis in the latter preparation as did its 7-hydroxy congener of the prior art. Intravenous infusion of this species of this invention in the DOCA-salt hypertensive and spontaneously hypertensive rats reduced blood pressure and heart rate. A similar but weaker effect on blood pressure and heart rate was observed with this compound in the renal hypertensive rat and in the normotensive rat tests. In conscious DOCA salt hypertensive rats, oral doses of 10 mg/kg of the di-n-propylaminoethyl compound demonstrated an anti-hypertensive effect. This species seems more readily absorbed from the gastrointestinal tract of rats than is its 7-hydroxy congener.

The pharmaceutical compositions of this invention which have pharmacodynamic activity within the cardiovascular system, for example renal vasodilatation, correcting hemodynamic imbalance, anti-anginal activity, hypotensive activity and bradycardia, are prepared in conventional dosage unit forms by incorporating a compound of formula I, or a pharmaceutically acceptable acid addition salt thereof, into a nontoxic pharmaceutical carrier according to accepted pharmacy procedures in a nontoxic quantity sufficient to produce the desired pharmacodynamic activity in a subject, animal or human. Preferably, the compositions will contain the active ingredient in an active but nontoxic quantity selected from the range of about 50 mg to about 500 mg, preferably about 75–250 mg, of active ingredient, as the base, per dosage unit. This quantity depends on the relative potency of the base compound compared with that of the prototypal species, 4-(2-di-n-propylaminoethyl)-2(3H)-indolone, as well as on the specific biological activity desired, the route of administration, that is, whether oral or parenteral, and the condition and size of the patient.

The pharmaceutical carrier employed for the dosage units is, for example, either a solid or liquid. Exemplary of solid carriers are lactose, terra alba, sucrose, talc, gelatin, agar, pectin, acacia, magnesium stearate or stearic acid. Exemplary of liquid carriers are isotonic saline for parenteral use or syrup, peanut oil, olive oil or water for soft gelatin capsules. Similarly, the carrier or diluent may include any time delay material well known to the art, such as cellulose esters or ethers and glyceryl esters alone or admixed with a wax. Such sustained release products as well as prodrug derivatives which may be gradually metabolized to the active parent can be employed to prolong the unique biological activity of the compounds of this invention or to attack receptors at a specific location.

A wide variety of pharmaceutical forms can be employed. Thus, if a solid carrier for oral or rectal administration is used, the mixed preparation can be tableted, placed in a hard gelatin capsule in powder or sustained release pellet form, in a suppository or in the form of a troche or lozenge. The amount of solid carrier will vary widely but, preferably, will be from about 25 mg to about 1 g. If a liquid carrier is used, the preparation will be in the form of a syrup, emulsion, soft gelatin capsule, sterile injectable liquid such as an ampul or an aqueous or nonaqueous liquid suspension for oral administration.

Advantageously, doses selected from the dosage unit ranges given above will be administered several times, such as from one to five times, a day. The daily dosage regimen is selected from the range of about 50 mg to about 1.0 g, preferably 200–750 mg for oral administration and 50–500 mg for parenteral administration. When the method described above is carried out, $D_2$-agonist activity is produced.

For an average size human using 4-(2-di-n-propylaminoethyl)-2(3H)-indolone hydrochloride as an active ingredient, a typical dose to show anti-hypertensive activity would be selected from the range of from about 100–250 mg of base equivalent for each dosage unit which is adapted for oral administration and which is administered orally from 1–4 times daily.

The following examples are designed solely to illustrate the preparation and use of the compounds of this invention. The temperatures are Centigrade. Other variations of these examples will be obvious to those skilled in the art.

EXAMPLE 1

A mixture of 3.44 g (9.63 mmoles) of 4-(2-di-n-propylaminoethyl)-7-hydroxy-2(3H)-indolone hydrobromide, 22 cc of dimethylformamide, 1.79 g (9.91 mmoles) of 5-chloro-1-phenyl-1H-tetrazole, 220 cc of acetone, 10 cc of water and 2.90 g (21 mmoles) of anhydrous potassium carbonate was refluxed for about 3 hours at which time thin layer chromatographic analysis (silica gel GF, 75:23:2 ethyl acetate-methanol-conc. ammonium hydroxide) indicated that the reaction was complete.

After cooling the reaction mixture in an ice-bath, the inorganic salts were removed by filtration and washed with acetone. The combined filtrates were concentrated in vacuo. The residual syrup was diluted with saturated brine and extracted with three portions of diethyl ether. The gathered extracts were dried over anhydrous magnesium sulfate, clarified with charcoal and treated with ethereal hydrogen chloride until precipitation was complete. The solid was slurried in diethyl ether and decanted several times, filtered and air-dried to give 3.8 g (86%) of tan 4-(2-di-n-propylaminoethyl)-7-(1-phenyl-1H-tetrazol-5-yloxy)-2(3H)-indolone hydrochloride. Recrystallization from 200 cc of hot acetonitrile gave 2.6 g (59%) of microcrystalline product, m.p. 245°–6°. Evaporation of the mother liquor and recrystallization of the residue from 25 cc of hot acetonitrile gave an additional 400 mg of product, m.p. 244°–5°.

A mixture of 2.64 g (5.78 mmoles) of the phenyl tetrazole ether, 200 cc of glacial acetic acid and 1.49 g of 10% palladium-on-carbon was hydrogenated in a Parr apparatus at moderate pressure for 20 hours at 50°. The warm reaction mixture was filtered through glass fiber filter paper and the catalyst washed thoroughly with hot glacial acetic acid. The filtrate was concentrated in vacuo, the pale yellow waxy residue distributed in water and ethyl acetate. After acidification of the aqueous phase with 3N hydrochloric acid, the organic phase was separated and extracted once with 1N hydrochloric acid. The combined aqueous phases were adjusted to pH 8.5 with aqueous 10% sodium hydroxide and extracted with a mixture of ethyl acetate and diethyl ether. The combined organic extract was back-washed once with saturated brine, dried over anhydrous magnesium sulfate, clarified with charcoal, treated with ethereal hydrogen chloride and evaporated to dryness in vacuo to give 1.64 g (96%) of pale yellow crystalline solid; 4-(2-di-n-propylaminoethyl)-2(3H)-indolone hydrochloride. Recrystallization from 260 cc of hot acetonitrile which was concentrated to about 50 cc gave 1.26 g (74%) of pale yellow microcrystalline powder, m.p. 240°–242°.

The hydrochloride salt (500 mg) is shaken in the presence of ether/5% sodium carbonate solution. The ether layer is separated, dried and evaporated to give the free base which is used to prepare other salt forms such as the methanesulfonate, ethanedisulfonate, sulfate or sulfamate salts by reacting aliquots of the base in ether with an excess of each acid.

EXAMPLE 2

A mixture of 22.0 g (0.105 mole) of 2-methyl-3-nitrophenylacetic acid and 25 cc of thionyl chloride was slowly heated to 75° and the copious evolution of gasses allowed to moderate. The temperature was raised and the solution was refluxed for 1 hour. The reaction was concentrated in vacuo. The residual straw-colored syrup was chased several times with dry toluene, diluted with 100 cc of dry toluene and added to a cool (10°) mixture of 13 g of sodium carbonate in 150 cc of water and 150 cc of toluene containing 14.5 cc (10.6 g, 0.12 mole) of di-n-propylamine with very slow stirring. After 30 minutes, the ice-bath was removed. Stirring was continued for one hour. An additional 0.5 g of solid sodium carbonate was added to the reaction. After 15 minutes, the organic phase was separated, washed with 5% aqueous sodium carbonate followed by 2N hydrochloric acid and, finally, water. The organic solution was dried over magnesium sulfate, concentrated in vacuo and pumped free of solvent to give 29.5 g of 2-methyl-3-nitrophenyl-N,N-di-n-propylacetamide as a straw-colored syrup.

The total syrup (105 mmoles) was taken up in 250 cc of anhydrous tetrahydrofuran and treated with 160 cc of 1.0M borane in tetrahydrofuran at room temperature for 1 hour. The reaction was refluxed for 2 hours, then cooled. Excess reagent was destroyed by the cautious addition of dry methanol. This solution was concentrated in vacuo. The residual syrup was treated with 40 cc of 6N hydrochloric acid for 1 hour on the steambath, cooled, basified with 40% sodium hydroxide and extracted with 3 portions of ether. The combined organic phase was washed once with brine, concentrated in vacuo and distilled in a Kugelrohr apparatus at 115°–118°/0.1 mm Hg to give 21.6 g of a mobile yellow oil; 2-methyl-3-nitrophenylethyl-N,N-di-n-propyl amine.

To a solution of 2.38 g (0.103 gram atoms) of sodium metal in 52 cc of absolute ethanol at room temperature was added 18.51 g (0.07 mole) of the nitro compound in one portion, with stirring, followed by 15.42 g (0.103 mole) of diethyl oxalate. The reaction was refluxed under nitrogen for about 20 minutes, cooled, quenched on 700 cc of ice-water and acidified with 3N hydrochloric acid. This aqueous solution was washed with a small volume of ether, basified to pH 8.5 with solid sodium carbonate and extracted with 3 portions of ether. The combined ether extract was washed with saturated brine, dried over anhydrous magnesium sulfate, clarified with charcoal and concentrated in vacuo. The residue was triturated with cold petroleum ether, filtered and air-dried to give 6.0 g of ethyl 6-(2-di-n-propylaminoethyl)-2-nitrophenylpyruvate as a yellow powder. The triturate was concentrated in vacuo and distilled to give 7.3 g of recovered starting material which was recycled. In the same manner, a total of three recycles provided 11.0 g of ethyl-6-(2-di-n-propylaminoethyl)-2-nitrophenylpyruvate.

A cold (10°) solution of 10.24 g (28.1 mmoles) of the pyruvate in 196 cc of 2% sodium hydroxide was treated with 5.0 cc of 30% hydrogen peroxide dropwise over several minutes. The cooling bath was removed and stirring was continued for 1.5 hours during which time the reaction became much lighter in color. A small amount of insoluble material was removed by filtration. The pH was adjusted to 1.5 by the cautious addition (foaming) of about 12 cc of conc. hydrochloric acid. This solution was concentrated in vacuo at 45°, reconstituted with water and evaporated twice more. The residue was slurried in a minimum volume of dilute hydrochloric acid, filtered and air-dried to give 6.40 g of 2-nitro-6(2-di-n-propylaminoethyl)-phenyl acetic acid hydrochloride as a white powder.

A mixture of 5.83 g (16.9 mmoles) of 2-nitro-6-(2-di-n-propylaminoethyl)-phenyl acetic acid hydrochloride and 0.6 g of 5% palladium-on-carbon in 250 cc of ethanol was hydrogenated at moderate pressure over 5.5 hours. The catalyst was filtered, washed with ethanol, and the filtrate evaporated to dryness in vacuo. The white residue was crystallized from 550 cc of hot acetonitrile to give 3.89 g of 4-(2-di-n-propylaminoethyl)-2(3H)-indolone hydrochloride, mp 240°–2°.

Anal. Calcd. for $C_{16}H_{24}N_2O$ HCl: C, 64.74; H, 8.49; N, 9.44. Found: C, 64.82; H, 8.26; N, 9.28.

EXAMPLE 3

A mixture of 2.73 g (10.0 mmoles) of 4-(2-aminoethyl)-7-hydroxy-2(3H)-indolone hydrobromide, 200 cc of dimethylformamide, 1.86 g (10.3 mmoles) of 5-chloro-1-phenyl-1H-tetrazole, 10 cc of water and 2.9 g (21 mmoles) of anhydrous potassium carbonate is stirred at room temperature for 2 days or until thin layer analysis indicates that no starting material remains. The reaction is filtered and the filtrate is acidified with dil. hydrochloric acid, concentrated in vacuo and the residue triturated with abs. ethanol. The triturate is clarified with charcoal and evaporated to dryness in vacuo. The hydrochloride salt of 4-(2-aminoethyl)-7-(1-phenyl-1H-tetrazol-5-yloxy)-2(3H)-indolone is hydrogenated directly in 200 cc of glacial acetic acid using 50% by substrate weight of 10% palladium-on-carbon at moderate pressure for 20 hours at 50°. The warm reaction mixture is filtered. The catalyst is washed thoroughly with hot acetic acid. After the filtrate is concentrated in vacuo, the residue is stripped several times from dilute hydrochloric acid and crystallized from ethanol to give 4-(2-aminoethyl)-2(3H)-indolone hydrochloride.

EXAMPLE 4

A mixture of 0.5 g of 4-(2-aminoethyl)-2(3H)-indolone hydrochloride, prepared as in Example 3, 2.2 g of isobutyraldehyde, 0.3 g of 5% palladium-on-charcoal and 75 ml of glacial acetic acid is hydrogenated at moderate pressure of hydrogen for 5 hours. The catalyst is separated by filtration and washed with acetic acid. The combined mother liquor-washings is evaporated in vacuo to give a residue which is taken up in cold methanol and treated with methanolic hydrogen bromide to give, upon concentration and cooling; 4-(2-diisobutylaminoethyl)-2(3H)-indolone hydrobromide.

EXAMPLE 5

A mixture of 0.9 g of 4-(2-aminoethyl)-2(3H)-indolone, 0.23 g of 4-benzyloxyphenylacetaldehyde, 0.25 g of 10% palladium-on-charcoal and 100 ml of ethanol is hydrogenated at 50 p.s.i. at 50° until the uptake of hydrogen is complete. After filtration, the mother liquors are evaporated to give 4-[2-(4-hydroxyphenethylamino)-ethyl]-2(3H)-indolone as the residue. This base in alcohol is treated with an excess of methanesulfonic acid to give the methanesulfonate salt.

Repeating this reaction with 4-n-propylaminoethyl-7-hydroxy-2(3H)-indolone and butyraldehyde gives 4-n-butyl-n-propylamino-ethyl-7-hydroxy-2(3H)-indolone hydrochloride.

EXAMPLE 6

Substituting 2.2 g of 4-(3-dimethylaminopropyl)-7-hydroxy-2(3H)-indolone hydrobromide (U.S. Pat. No. 4,314,944) for 4-(2-di-n-propylaminoethyl)-7-hydroxy-2(3H)-indolone hydrobromide in Example 1 gives 4-(3-dimethylaminopropyl)-7-(1-phenyl-1H-tetrazol-5-yloxy)-2(3H)-indolone hydrochloride and, then, 4-(3-dimethylaminopropyl)-2(3H)-indolone base as well as the ethanedisulfonate salt as described above.

Substituting 4-n-propylaminoethyl-7-hydroxy-2(3H)-indolone hydrobromide gives 4-n-propylaminoethyl-2-(3H)-indolone hydrochloride.

Substituting 4-dimethylaminopropyl-7-hydroxy-2(3H)-indolone hydrobromide gives 4-dimethylaminopropyl-2(3H)-indolone hydrochloride.

EXAMPLE 7

4-Aminoethyl-2(3H)-indolone (10 g) is reacted with two mole equivalents of allyl bromide and 4 equivalents of triethylamine in acetonitrile with mild heat for several hours. The reaction mixture is evaporated. The residue is suspended in water. The mixture is extracted with ethyl acetate. The extracts are washed, dried and evaporated to give 4-di-allylaminoethyl-2(3H)-indolone. This material (1 g) is dissolved in ether-ethanol and treated with methanesulfonic acid to give the methane sulfonate salt. Using benzyl bromide gives 4-dibenzylaminoethyl-2(3H)-indolone.

EXAMPLE 8

Anhydrous tetrahydrofuran (10 cc) at 20° under nitrogen was treated with 2.0 cc (4.8 mmoles) of 2.4M n-butyl lithium in hexane followed by 0.49 g (1.5 mmoles) of 4-di-n-propylaminoethyl-7-methoxy-2(3H)-indolone hydrochloride and 0.349 g (3 mmoles) of N,N,N',N'-tetramethylethylene diamine. Gas evolution and dissolution of the salt was observed.

The reaction mixture was cooled in a dry ice-propanol bath and treated with 1.5 mmoles of iodomethane in one portion. After stirring in the cold for 10 minutes, the bath was removed and stirring continued for 2 hours. The mixture was quenched in 20 cc of saturated ammonium chloride solution, diluted with ethyl ether. The organic layer was separated. The remaining material was again extracted twice. The combined dried extracts were concentrated in vacuo, stripped from ethyl ether and carbon tetrachloride.

Analysis of the solid demonstrated a mixture of 10% starting material and a 50-50 mixture of di- and mono 3-methylated product. The mixture was realkylated to give 169 mg of 3,3-dimethyl-4-di-n-propylaminoethyl-7-methoxy-2(3H)-indolone.

This material is hydrolyzed using boron tribromide, then, dehydroxylated in the form of the crude product as described above to give 3,3-dimethyl-4-di-n-propylaminoethyl-2(3H)-indolone hydrochloride.

The C-alkylation process was repeated using the same quantities but using 0.61 cc (9.8 mmoles) of methyl iodide at −70°. The mixture was allowed to warm to −25° and held there for 1 hour followed by 3 hours at room temperature. After working up as described, 4-di-n-propylaminoethyl-7-methoxy-3-methyl-2(3H)-indolone was recovered. This is treated with boron tribromide and, then, 5-chloro-1-phenyl-1H-tetrazole to give 4-di-n-propylaminoethyl-3-methyl-2(3H)-indolone hydrochloride.

EXAMPLE 9

3-Nitro-2-methyl-phenylacetic acid, 20.0 g (0.102 mole), was mixed with 250 cc of methylene chloride to which was added a solution in methylene chloride (10 to 1) of thionyl chloride (34.99 g, 0.294 mole). The mixture was refluxed for 2½ hours at which time the starting material was no longer detectable by infrared analysis.

The solution was concentrated in vacuo to an oil Toluene was added and the mixture was reconcentrated to an oil. This was dissolved in 150 cc of toluene.

Into a 2 l beaker was placed 400 cc of water, 200 cc of toluene, 35.35 g (0.256 mole) of potassium carbonate and 23.54 g, (0.102 mole) of N-n-propyl-N-4-methoxyphenethylamine. This solution was stirred. This amine was prepared by N-acylation of 4-methoxyphenethylamine using propionyl chloride followed by boron hydride reduction of the resulting amide.

The toluene solution of the acid chloride was added dropwise. The mixture was vigorously stirred. Stirring continued over the weekend.

The toluene layer was separated and the aqueous mixture was extracted with toluene. The combined toluene layers were dried over magnesium sulfate and filtered. TLC (silica gel GF plates; chloroform/methanol): rf=0.70–0.80, traces at 0.45, 0.00–0.05; the last fraction was positive to ninhydrin.

The solution was concentrated to an oil; 39.06 g of N-4-methoxyphenethyl-N-n-propyl-2-methyl-3-nitrophenylacetamide.

Gas chromatographic analysis indicated 97% purity. A single impurity was seen.

NMR indicated toluene traces. The oil was placed under high vacuum at ambient temperature to give 35.76 g, 96.6 mmoles, 94.7% of amide.

The acetamide (35.75 g, 96.6 mmoles) was dissolved in 250 cc of tetrahydrofuran and stirred. To this was added borane in tetrahydrofuran, (0.193 mole). The addition was dropwise and without noticeable exotherm. The reaction mixture was stirred.

An aliquot was removed, diluted with methanol (gaseous evolution) and boiled to a small volume,. TLC (chloroform/methanol): starting material rf=0.80–0.90; trace 0.70; reaction mixture rf=0.40–0.50, minor 0.90. GLC indicated no starting material present.

The majority of the solvent was then removed in vacuo and the flask was cooled in an ice bath. About 500 cc of methanol was added and the reaction mixture was reduced to a small volume. The remaining oil was diluted with ether to give a cloudy solution. This solution was filtered, and the ether solution was saturated with hydrogen chloride gas to give crystals which then oiled.

The material which oiled was dissolved in ethanol.

The oil was mixed with 5% sodium carbonate and ether. There was slow solubility, and some insoluble material. The ethereal solution was dried (total volume of 400 cc) and concentrated to an oil, 31.5 g.

The oil was subjected to distillation . Material distilled at 200°/1.5 mm as an amber oil, 18.74 g.

Distillation was then resumed. An additional 9.7 g was obtained of a darker amber oil.

TLC (chloroform/methanol 9:1) on the first fraction: rf=0.65–0.80; positive to ninhydrin. The fractions were transferred: Fraction 1, 18.4 g, Fraction 2, 8.96 g. Total yield of fractions 1 and 2, 27.36 g, (79.5%) of N-n-propyl-N-4-methoxyphenethyl-3-nitro-2-methylphenethylamine.

A 50 cc 3 neck flask was dried and purged with dry nitrogen. To this was added about 10 cc of ether and 1.1 g (28 mmoles) of potassium metal in large chunks. The mixture was stirred.

To this was added a mixture of 8.3 cc of absolute ethanol and 6.7 cc of ether. The addition was accompanied by an exotherm. After 2.5 hours, additional ether was added as the solution was extremely viscous. There was no potassium metal present after 20 minutes of stirring following the ether addition.

Diethyl oxalate (3.8 cc, 20 moles) was added in a single portion. The mixture became a slightly darker yellow. This solution was stirred for about 15 minutes.

The amine (10.0 g, 28 mmoles) dissolved in a slight amount of ether was added portionwise. The mixture turned a noticeable purple color. The solution was stirred for 30 minutes, then stoppered and allowed to stand overnight.

About 10 cc of water and 10 cc of ether were added. The mixture was stirred for one hour. The mixture was diluted with water (300 cc) and extracted with ether. The extract was washed with brine. The brine solution was added to the aqueous layer. This caused a dark oil to separate from the aqueous solution. The pH of the solution was about 8. In case the oil contained unhydrolyzed ester, the mixture (aqueous plus oil) was diluted with 75 cc of 12% sodium hydroxide solution and stirred for one hour. The solution was extracted with ether and, then, acidified with 10% hydrochloric acid. An oil/gum formed which was extracted with chloroform. The extract was washed with brine and dried. The extract was filtered. TLC (ethyl acetate/methanol/ammonia, 75:23:2); rf=0.55–0.60 major, 0.80, 0.40, 0.35, 0.00, all traces; recrystallized reference material, rf=0.55–0.60.

Concentration in vacuo caused severe frothing, so the solution was primarily concentrated by heating under a stream of nitrogen. Final concentration in vacuo gave a buff colored foam. The foam was triturated with ether and filtered to give 5.5 g of buff powder. Trituration of a small portion with ethylacetate gave crystals, m.p. 174°(d).

The 5.5 g powder and 5.25 g powder (from another preparation) were combined, and triturated with boiling ethyl acetate (300 cc). There was some blackish gummy material which remained intractable. The solution was decanted and concentrated to 100 cc, then chilled to give a solid precipitate which was filtered and washed with cold ethyl acetate. Upon exposure to suction filtration, the crystals slowly darkened from a light tan to a brown. The material also became gummy. The material was taken up in methylene chloride and filtered.

The solution was concentrated to 150 cc. Dilution of a small aliquot with ether gave light colored crystals. On a larger scale, the material gummed. The small-aliquot crystalline portion was heated at 24° in vacuo for one hour.

The gummed material was triturated with ether to give light brown crystals, with some dark solid particles present. The powder (8.73 g) was air dried to give 8.32 g. The material was isolated as the hydrochloride salt of the substituted pyruvic acid.

The pyruvic acid (5.0 g, 10.7 mmoles) was stirred in 50 cc of freshly prepared 20% sodium hydroxide. The solution was cooled to 10° in an ice bath. Hydrogen peroxide (3.03 cc of 30% solution, 27 mmoles) was added with an exotherm to 18°. The temperature slowly cooled to 4°.

The mixture was stirred. After ½ hour, an additional 1.0 cc of 30% peroxide was added (9 mmoles). After an additional 30 minutes of stirring, the mixture was acidified with concentrated hydrochloric acid giving initially crystals which gummed. The mixture was extracted with methylene chloride. The extract was washed with brine, dried and filtered. The solution was concentrated to a foam (4.9 g) and combined with 3.2 g from another preparation.

The combined fractions were filtered in an ether slurry. Then, the material was dissolved in dilute sodium hydroxide, filtered, and extracted with methylene chloridechloroform which tended to form an emulsion. The emulsion broke and the methylene chloridechloroform layer was separated and dried. TLC indicated a single component—the desired phenylacetic acid. The solution was filtered, then the filtrate was concentrated to a foam (4.4 g).

The acetic acid compound (9.9 mmoles, 4.15 g) was mixed with 500 mg of 5% palladium-on-charcoal and diluted with 250 cc of ethanol. To this was added 1.0 cc of 12N hydrochloric acid (12 mmoles). The mixture was shaken on a Parr hydrogenator under hydrogen at moderate pressure.

The catalytic reduction proceeded sluggishly, requiring isolation of partly reduced material and further reduction with fresh 5% palladium catalyst in ethanol acidified with hydrochloric acid. Ultimately, this reaction mixture was heated to 50° and shaken under moderate hydrogen pressure for several hours. Thin layer chromatographic analysis (silica gel GF using chloroform/methanol, 4:1) indicated a mixture of two products was formed. These were separated by chromatography on 150 g of silica gel 60 mesh using chloroform/methanol, 95:5 as the eluent. The desired product was eluted in fractions 8–41 (20 cc each) and gave 1.0 g on concentration of the combined solutions. Rechromatography of fractions 42–67 (2.5 g) using a similar system but eluting with chloroform (100%) gave 0.88 g from combined fractions 47-101 (10 cc each). These two materials were combined and recrystallized from acetonitrile to give 0.99 g, (m.p. 156°–158°) of 4-(N-n-propyl-N-4-methoxyphenethylaminoethyl)-2(3H)-indolone.

The indolone (2.0 g, 2.57 mmoles) was mixed with 20 cc of 48% hydrobromic acid. After stirring at reflux for 3 hours, the mixture was transferred to a larger flask with the aid of methanol and concentrated in vacuo to an oil.

After 4 triturations with acetone and concentration in vacuo a buff foam, (1.2 g) of 4-[N-n-propyl-N-(4-hydroxyphenethyl)-2-aminoethyl]-2(3H)-indolone hydrobromide was obtained. TLC silica gel GF/(chloroform/methanol, 4:1): starting material rf=0.65; reaction product rf=0.55 recrystallized yield 0.95 g, m.p. over 175° (d.).

The base is formed by shaking 500 mg of product in ether/chloroform/acqueous sodium carbonate and isolation from the organic layer. It is converted to the methanesulfonic acid and hydrochloric acid salts by reaction with an excess of each acid in etherchloroform.

EXAMPLE 10

4-(2-di-n-Propylaminoethyl)-2(3H)-indolone hydrochloride (125 mg) is mixed with 200 mg of lactose and 2 mg of magnesium stearate, filled into a hard gelatin capsule and administered to an anginal or hypertensive human patient from 1–3 times daily.

What is claimed is:

1. The method of treating hypertension, angina pectoris, congestive heart failure or kidney dysfunction by inducing $D_2$-receptor agonist activity comprising administering orally, rectally or parenterally to a patient subject to one of these abnormal conditions a nontoxic, active therefor quantity of a compound of the structural formula;

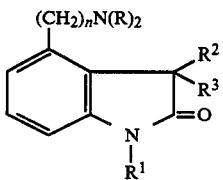

in which:

R is, each, hydrogen, lower alkyl, benzyl, allyl, phenethyl or 4-hydroxyphenethyl;

$R^1$, $R^2$ and $R^3$ are each hydrogen or $C_{1-4}$-lower alkyl; and n is 1, 2 or 3; or a pharmaceutically acceptable acid addition salt thereof, in dosage unit form, combined with a pharmaceutical carrier.

2. The method of claim 1 in which the compound is 4-(2-di-n-propylaminoethyl)-2(3H)-indolone or a pharmaceutically active acid addition salt thereof.

3. The method of claim 1 in which the compound is 4-(2-di-n-propylaminoethyl)-2(3H)-indolone hydrochloride.

4. The method of claim 8 in which the compound is 4-[N-n-propyl-N-(4-hydroxyphenethyl)-2-aminoethyl]-2-(3H)-indolone or a pharmaceutically acceptable, acid addition salt thereof.

5. The method of claim 1 in which the compound is administered orally or parenterally from 1 to 5 times daily in the form of a dosage unit containing a quantity of the compound selected from the range of 50–500 mg.

6. The method of claim 5 in which a quantity selected from 75–250 mg per dosage unit is administered from 1-5 times daily.

7. The method of claim 1 in which $R^1$, $R^2$ and $R^3$ are each hydrogen.

8. The method of claim 6 in which the patient is hypertensive.

9. The method of claim 6 in which the patient has angina pectoris.

10. The method of claim 6 in which the patient has the symptoms of congestive heart failure.

11. 4-[N-n-Propyl-N-(4-hydroxyphenethyl)-2-aminoethyl]-2(3H)-indolone or a pharmaceutically acceptable, acid addition salt thereof.

12. The compound of claim 11 as the hydrochloride salt.

13. The compound of claim 11 as the methanesulfonic acid salt.

* * * * *